US011354933B2

(12) United States Patent
Lee et al.

(10) Patent No.: US 11,354,933 B2
(45) Date of Patent: Jun. 7, 2022

(54) WEARABLE DEVICE AND METHOD FOR ESTIMATING BIO-INFORMATION

(71) Applicant: SAMSUNG ELECTRONICS CO., LTD., Suwon-si (KR)

(72) Inventors: Jong Wook Lee, Suwon-si (KR); Sang Yun Park, Hwaseong-si (KR); Byung Hoon Ko, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/951,059

(22) Filed: Nov. 18, 2020

(65) Prior Publication Data

US 2021/0365664 A1 Nov. 25, 2021

(30) Foreign Application Priority Data

May 22, 2020 (KR) .................. 10-2020-0061606

(51) Int. Cl.
| | |
|---|---|
| *G06V 40/12* | (2022.01) |
| *G06F 3/041* | (2006.01) |
| *A61B 5/00* | (2006.01) |
| *A61B 5/021* | (2006.01) |
| *G06V 40/60* | (2022.01) |

(Continued)

(52) U.S. Cl.
CPC ...... *G06V 40/1365* (2022.01); *A61B 5/02116* (2013.01); *A61B 5/442* (2013.01); *A61B 5/681* (2013.01); *G06F 3/0412* (2013.01); *G06F 3/04146* (2019.05); *G06V 40/1306* (2022.01); *G06V 40/67* (2022.01);

(Continued)

(58) Field of Classification Search
CPC .......... G06K 9/00087; G06K 9/00912; G06K 9/0002; G06K 2009/00932; G06K 2009/00939; A61B 5/02116; A61B 5/681; A61B 5/442; G06F 3/0412; G06F 3/04146; G06F 2203/04105
See application file for complete search history.

(56) References Cited

U.S. PATENT DOCUMENTS

| | | | |
|---|---|---|---|
| 6,342,284 B1 | 1/2002 | Yu et al. | |
| 6,632,550 B1 | 10/2003 | Yu et al. | |

(Continued)

FOREIGN PATENT DOCUMENTS

| | | |
|---|---|---|
| JP | 2017-70630 A | 4/2017 |
| KR | 10-2019-0030152 A | 3/2019 |

(Continued)

OTHER PUBLICATIONS

Anand Chandraseklar et al., "Smartphone-based blood pressure monitoring via the oscillometric fingerpressing method", Science Translational Medicine, vol. 10, eaap8674, Mar. 7, 2018, pp. 1-11 (12 pages total).

*Primary Examiner* — Edward F Urban
*Assistant Examiner* — Wassim Mahrouka
(74) *Attorney, Agent, or Firm* — Sughrue Mion, PLLC

(57) ABSTRACT

A wearable device may include a main body, a sensor formed on a stem disposed on a side of the main body, and configured to acquire a partial fingerprint image of a finger of a user based on the finger being in contact with the sensor, and a processor configured to control a display to guide the user based on the acquired partial fingerprint image and a full fingerprint image of the finger to permit a measurement site of the finger to contact the sensor.

25 Claims, 19 Drawing Sheets

(51) Int. Cl.
  *G06V 40/13* (2022.01)
  *G06V 40/14* (2022.01)
  *G06V 40/10* (2022.01)
(52) U.S. Cl.
  CPC .... *G06F 2203/04105* (2013.01); *G06V 40/14* (2022.01); *G06V 40/15* (2022.01)

(56) References Cited

U.S. PATENT DOCUMENTS

| | | | |
|---|---|---|---|
| 6,800,131 | B2 | 10/2004 | Yu et al. |
| 7,244,304 | B2 | 7/2007 | Yu et al. |
| 7,425,236 | B2 | 9/2008 | Yu et al. |
| 7,758,980 | B2 | 7/2010 | Yu et al. |
| 7,964,034 | B2 | 6/2011 | Yu et al. |
| 8,142,914 | B2 | 3/2012 | Yu et al. |
| 8,303,709 | B2 | 11/2012 | Yu et al. |
| 8,500,904 | B2 | 8/2013 | Yu et al. |
| 8,974,597 | B2 | 3/2015 | Yu et al. |
| 10,398,324 | B2 | 9/2019 | Mukkamala et al. |
| 10,866,619 | B1* | 12/2020 | Bushnell ................ G06F 1/163 |
| 2002/0045074 | A1 | 4/2002 | Yu et al. |
| 2014/0003679 | A1* | 1/2014 | Han ..................... G06K 9/0002 382/124 |
| 2015/0131876 | A1* | 5/2015 | Chang .................. G06F 3/0488 382/124 |
| 2015/0186705 | A1* | 7/2015 | Magi ....................... G06F 1/163 382/125 |
| 2015/0242696 | A1* | 8/2015 | Kim .................. G06K 9/00013 345/173 |
| 2017/0251935 | A1* | 9/2017 | Yuen .................... A61B 5/0261 |
| 2017/0364730 | A1* | 12/2017 | Jiang .................. G06K 9/00026 |
| 2018/0074643 | A1* | 3/2018 | Tushar Balasaheb ...................... G06F 21/316 |
| 2018/0082102 | A1* | 3/2018 | Lee .................... G06K 9/00013 |
| 2018/0177413 | A1* | 6/2018 | Kwon ................ A61B 5/02108 |
| 2018/0199831 | A1 | 7/2018 | Kawachi et al. |
| 2019/0059751 | A1 | 2/2019 | Huang et al. |
| 2019/0076032 | A1 | 3/2019 | Park et al. |
| 2019/0239758 | A1 | 8/2019 | Park et al. |
| 2019/0274555 | A1 | 9/2019 | Park et al. |
| 2020/0019745 | A1 | 1/2020 | Kang et al. |
| 2021/0004561 | A1* | 1/2021 | Xu .................... G06K 9/00013 |

FOREIGN PATENT DOCUMENTS

| | | |
|---|---|---|
| KR | 10-2019-0094730 A | 8/2019 |
| KR | 10-2019-0107473 A | 9/2019 |
| KR | 10-2019-0117100 A | 10/2019 |
| KR | 10-2020-0007312 A | 1/2020 |
| WO | 2019/148872 A1 | 8/2019 |
| WO | 2020/006518 A1 | 1/2020 |

\* cited by examiner

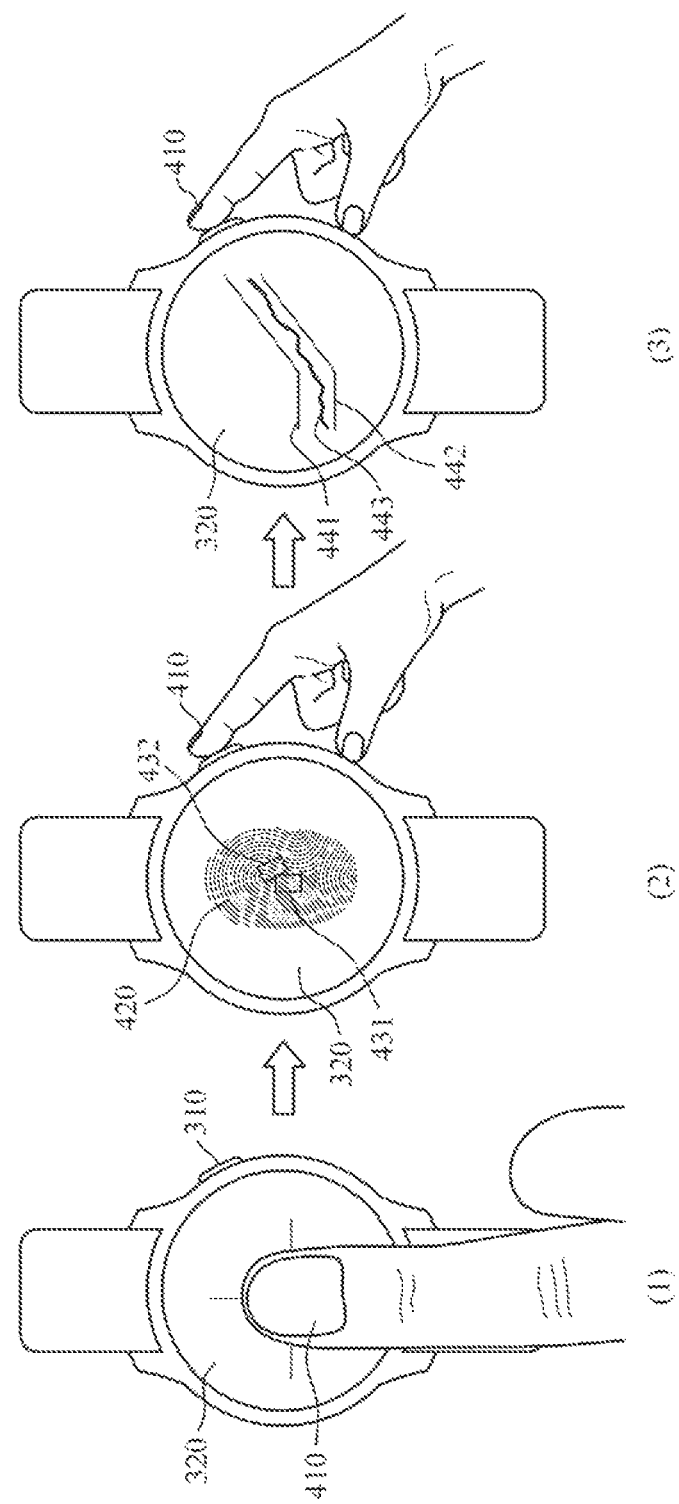

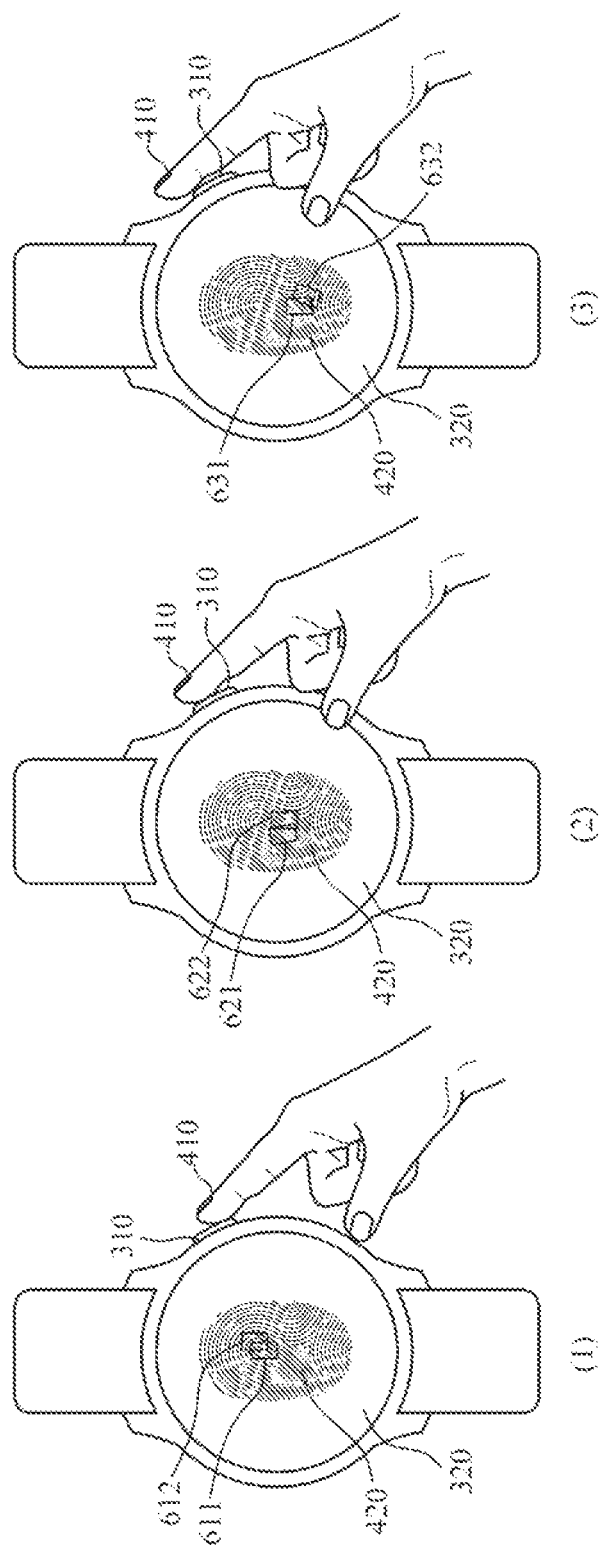

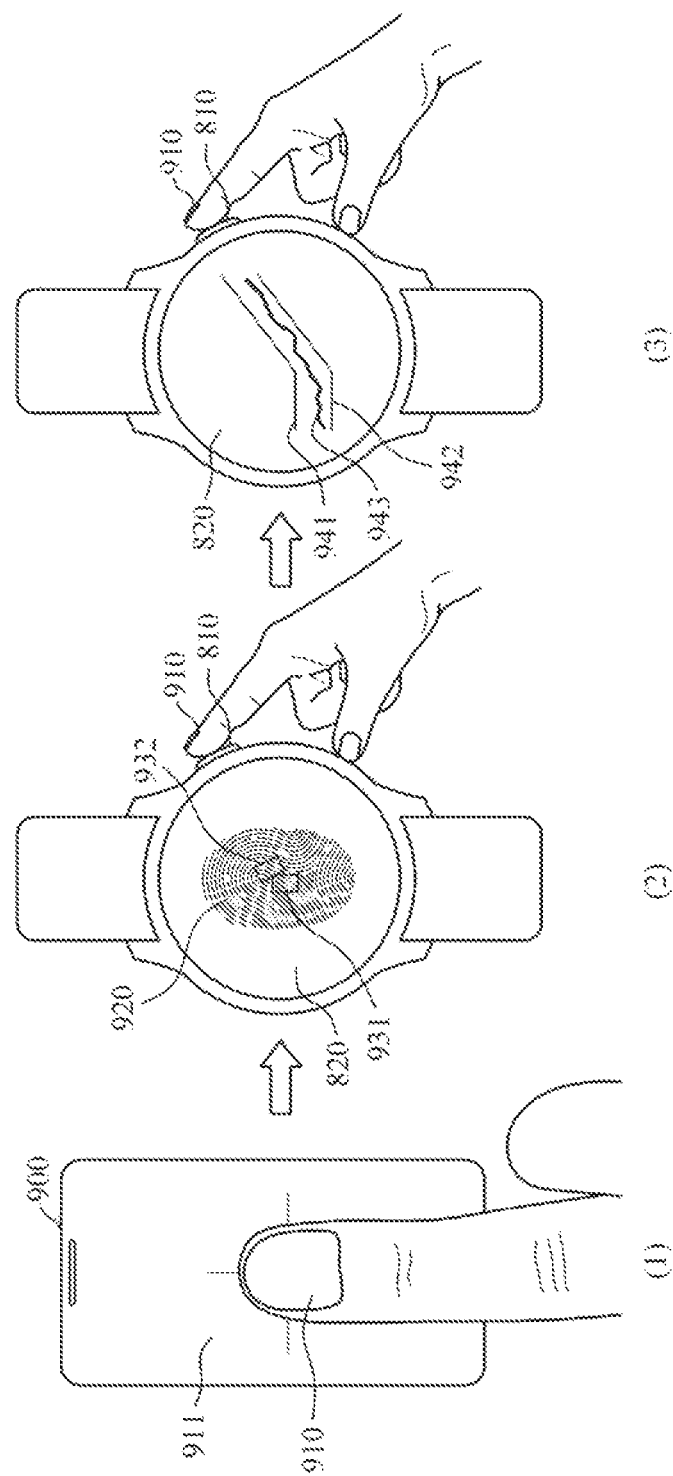

WEARABLE DEVICE AND METHOD FOR ESTIMATING BIO-INFORMATION

CROSS-REFERENCE TO RELATED APPLICATION(S)

This application is based on and claims priority under 35 U.S.C. § 119 to Korean Patent Application No. 10-2020-0061606, filed on May 22, 2020, in the Korean Intellectual Property Office, the disclosure of which is incorporated by reference herein in its entirety.

BACKGROUND

1. Field

The following description relates to a wearable device and a technology for estimating bio-information in the wearable device.

2. Description of Related Art

Recently, smartphones and wearable devices have become popular, and health index measurement using such devices has drawn a great deal of attention. In general, main applications of such devices are measurement of the number of steps, an amount of activity, and the like, using an acceleration sensor, and measurement of heart rate using a heart rate sensor, but, in recent years, an interest in medically more important indicators, such as arrhythmia, blood pressure, blood sugar, etc., which are measured using an electrocardiogram sensor, or the like, is growing.

Methods of estimating blood pressure using a smartphone or a wearable device mainly include a pulse wave analysis (PWA) method of analyzing a shape of a photoplethysmography (PPG) waveform, a method of measuring a speed of pulse wave using a pulse transit time (PTT) or a pulse arrival time (PAT) and estimating blood pressure using the measured speed, an oscillometry method of measuring amplitude of a pulse wave while pressing the entire or part of a measurement site, and the like. Generally, the methods of estimating blood pressure using PWA, PTT, PAT, and the like, need to periodically perform calibration, and thus are usually applied to trend tracking. The oscillometry method is advantageous in that it can estimate an absolute blood pressure level.

In general, it is known that a finger is made up of a structure similar to that of an upper arm and hence is effective for measuring blood pressure using an oscillometry method. However, since skin, fat, bone, blood vessels, and the like, are complexly located in a small area of the finger unlike the upper arm of a large area, it is important to accurately align the position and direction of a sensor when performing oscillometry.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an example embodiment, a wearable device may include a main body; a sensor formed on a stem disposed on a side of the main body, and configured to acquire a partial fingerprint image of a finger of a user based on the finger being in contact with the sensor; and a processor configured to control a display to guide the user based on the acquired partial fingerprint image and a full fingerprint image of the finger to permit a measurement site of the finger to contact the sensor.

The sensor may include a finger contact surface configured to contact the finger, a light sensor configured to emit light to the finger in contact with the finger contact surface and detect light scattered or reflected from the finger, and a force sensor configured to measure a contact force between the finger and the finger contact surface.

The wearable device may further include the display disposed on a surface of the main body. The processor may control the display to display the full fingerprint image of the finger, and display a marker indicating the measurement site of the finger on the displayed full fingerprint image.

The processor may determine whether the measurement site of the finger is in contact with the sensor based on the full fingerprint image and the partial fingerprint image; and based on determining that the measurement site of the finger is not in contact with the sensor, control the display to display a marker indicating a current measurement site of the finger on the full fingerprint image displayed.

The processor may determine a site matching the partial finger print image from the full fingerprint image; and compare a fingerprint image of the determined site with a fingerprint at a position where the marker indicating the measurement site is located to determine whether the measurement site of the finger is in contact with the sensor.

The processor may control the display to guide a contact pressure between the finger and the sensor based on determining that the measurement site of the finger is in contact with the sensor.

The processor may acquire pulse wave signals from a plurality of target measurement sites through the sensor and determine the measurement site of the finger based on the acquired pulse wave signals.

The processor may control the display to display the full fingerprint image of the finger and display a marker indicating the measurement site of the finger on the displayed full fingerprint image.

The wearable device may further include the display disposed on a surface of the main body. The display may include a fingerprint sensor, and the processor may acquire the full fingerprint image of the finger using the fingerprint sensor of the display.

The processor may control the display to display a marker indicating a region of the fingerprint sensor on the display to permit the user to bring the finger into contact with the fingerprint sensor.

The processor may control the display to display a marker for specifying a reference measurement site of the finger based on the finger being in contact with a position of the marker indicating the fingerprint sensor.

The processor may control the display to display text for guiding the user to move the finger in order to acquire the full fingerprint image based on the user moving the marker for specifying the reference measurement site of the finger to the reference measurement site.

The wearable device may further include a communication interface configured to receive, from an external device, the full fingerprint image acquired in advance from the finger of the user.

The processor may estimate bio-information based on a pulse wave signal and a contact force based on the sensor acquiring the pulse wave signal and the contact force from the measurement site of the finger.

The bio-information may include one or more of a blood pressure, a vascular age, an arterial stiffness, an aortic artery pressure waveform, a vascular elasticity, a stress index, and a fatigue level.

According to an aspect of an example embodiment, a wearable device may include a main body; a sensor formed on a stem disposed on a side of the main body and configured to acquire a partial fingerprint image of a finger of a user based on the finger being in contact with the sensor; a communication interface mounted in the main body; and a processor configured to: transmit the partial fingerprint image to an external device to permit the external device to guide the user to permit a measurement site of the finger to contact the sensor, based on the acquired partial fingerprint image and a full fingerprint image of the finger; and control the sensor to acquire a pulse wave signal based on the measurement site of the finger being in contact with the sensor.

The processor may estimate bio-information based on the pulse wave signal and a contact force based on the sensor acquiring the pulse wave signal and the contact force from the measurement site of the finger.

According to an aspect of an example embodiment, a method of estimating bio-information by a wearable device may include acquiring a partial fingerprint image of a finger based on the finger of a user being in contact with a sensor formed on a stem disposed on a side of a main body of the wearable device; and guiding the user based on the acquired partial fingerprint image and a full fingerprint image of the finger to permit a measurement site of the finger to contact the sensor.

The method may include displaying the full fingerprint image of the finger and a marker indicating the measurement site of the finger on a display of the wearable device.

The guiding may include determining whether the measurement site of the finger is in contact with the sensor based on the full fingerprint image and the partial fingerprint image; and based on determining that the measurement site of the finger is not in contact with the sensor, displaying a marker indicating a current measurement site of the finger on the full fingerprint image displayed on the display.

The determining may include determining a site matching the partial finger print image from the full fingerprint image and comparing a fingerprint image of the determined site with a fingerprint at a position where the marker indicating the measurement site is located.

The method may include guiding a contact pressure between the finger and the sensor based on determining that the measurement site of the finger is in contact with the sensor.

The method may include determining the measurement site of the finger based on pulse wave signals acquired from a plurality of target measurement sites of the finger.

The method may include acquiring the full fingerprint image of the finger.

The method may include acquiring, by the sensor, a pulse wave signal and a contact force from the measurement site of the finger; and estimating bio-information based on the acquired pulse wave signal and contact force.

Other features and aspects will be apparent from the following detailed description, the drawings, and the claims.

BRIEF DESCRIPTION OF THE DRAWINGS

FIG. 4 is a diagram illustrating an embodiment of guiding a measurement site of a finger;

FIGS. 6A to 6C are diagrams illustrating an embodiment of determining and guiding an optimal measurement site of a finger;

FIGS. 9A and 9B are diagrams illustrating another embodiment of determining an optimal measurement site of a finger;

Figure 1:
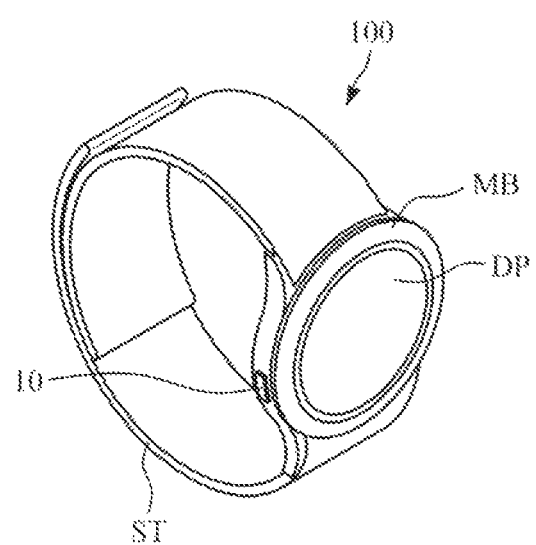
FIG. 1 is a diagram illustrating a wearable device according to an embodiment.

Throughout the drawings and the detailed description, unless otherwise described, the same drawing reference numerals will be understood to refer to the same elements, features, and structures. The relative size and depiction of these elements, features, and structures may be exaggerated for clarity, illustration, and convenience.

DETAILED DESCRIPTION

Details of exemplary embodiments are provided in the following detailed description with reference to the accompanying drawings. The disclosure may be understood more readily by reference to the following detailed description of exemplary embodiments and the accompanying drawings. The disclosure may, however, be embodied in many different forms and should not be construed as being limited to the embodiments set forth herein. Rather, these embodiments are provided so that the disclosure will be thorough and complete and will fully convey the concept of the invention to those skilled in the art, and the disclosure will only be defined by the appended claims. Like reference numerals refer to like elements throughout the specification.

It will be understood that, although the terms "first," "second," etc. may be used herein to describe various elements, these elements should not be limited by these terms. These terms are used to distinguish one element from another. Also, the singular forms of terms are intended to include the plural forms of the terms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as "unit" and "module" denote units that process at least one function or operation, and they may be implemented by using hardware, software, or a combination of hardware and software.

Figure 2A:
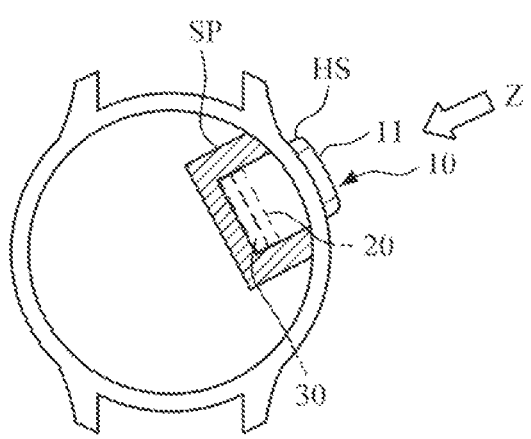
FIGS. 2A to 2C are diagrams illustrating embodiments of a structure of a sensor of a wearable device.
Figure 2B:
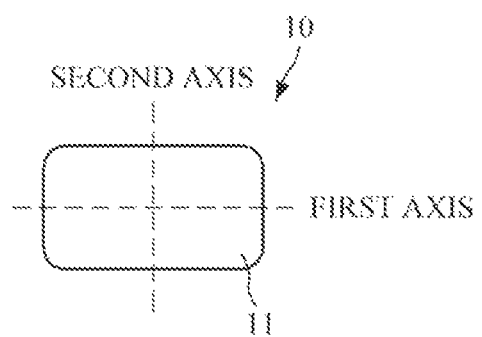
Figure 2C:
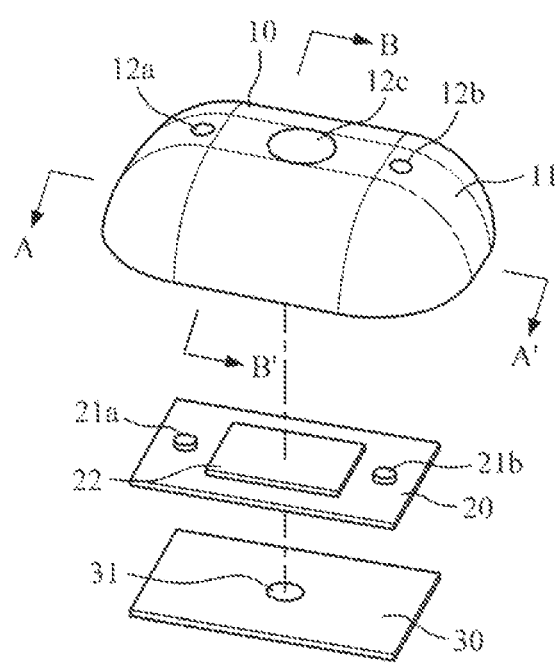

FIG. 1 is a diagram illustrating a wearable device according to an embodiment. FIGS. 2A to 2C are diagrams illustrating embodiments of a structure of a sensor of a wearable device. Embodiments of the wearable device 100 may be fabricated in the form of a smartwatch or a smart band. However, the wearable device 100 is not limited thereto.

Referring to FIG. 1, the wearable device 100 includes a main body MB and a strap ST.

The main body MB may include various modules configured to perform various functions of the wearable device 100. A battery may be embedded in the main body MB or the strap ST to supply power to various modules. The strap ST may be connected to the main body MB. The strap ST may be flexible so as to be bent around a user's wrist. The strap ST may include a first strap and a second strap that is separated from the first strap. Respective ends of the first and second straps are connected to both sides of the main body MB, and the first strap and the second strap may be fastened to each other using fasteners formed on the other sides thereof. In this case, the fasteners may be formed as Velcro fastening, pin fastening, or the like, but are not limited thereto. In addition, the strap ST may be formed as an integrated piece, such as a band.

A display DP may be disposed on a surface of the main body MB to visually display various types of information. The display DP may include a touch screen panel for touch input by a user. Also, the display DP may include an on-screen fingerprint sensor for recognition of a user's fingerprint.

A sensor 10 for measuring various signals from the user's finger may be formed on a stem disposed in the form of a button on a side of the main body MB. The sensor 10 may operate in bio-information estimation mode or in normal mode under the control of a processor. In the bio-information estimation mode, the sensor 10 may acquire a pulse wave signal from a finger by detecting light reflected or scattered from the finger when the finger touches the sensor 10. Also, the sensor 10 may acquire information on force applied by contact with the finger. In the normal mode, the sensor 10 may serve a user interface function for controlling general functions of the wearable device 100, for example, selection/execution of an application, graphical user interface (GUI) adjustment of the display DP, etc.

Referring to FIG. 2A, the sensor 10 may include a housing HS. The sensor 10 may include a light sensor 20 and a force sensor 30, which are disposed inside the housing HS or at a lower part of the housing HS.

A part of the housing HS is in the form of a button, which is exposed to the outside through the side of the main body MB. For example, a support SP inside the main body MB may support the housing HS from at least one of a periphery and a lower part of the housing HS. In the embodiment of FIG. 2A, the support SP is illustrated as enclosing the housing HS inside the main body MB, but this is merely an example and the embodiment is not limited thereto. Although not illustrated in FIG. 2A, an additional structure for preventing the housing HS from being dislodged to the outside of the main body MB may be further included in the housing HS or the main body MB.

The housing HS may include a finger contact surface 11 which is in contact with a finger put thereon. FIG. 2B illustrates an example of a shape of the finger contact surface 11 (hereinafter referred to as a "plan view") when the sensor 10 of FIG. 2A is viewed in a direction (Z direction) perpendicular to the finger contact surface 11. In the plan view of the finger contact surface 11, a first axis traversing the center of the finger contact surface 11 may be a long axis and a second axis traversing the center of the finger contact surface 11 in a different direction from that of the first axis may be a short axis. The first axis and the second axis may be perpendicular to each other. Although not illustrated, in another example, the plan view of the finger contact surface 11 may have the first and second axes that are equal in length. In addition, in FIG. 2B, the plan view of the finger contact surface 11 is illustrated as a rectangular shape with rounded corners, but the plan view of the finger contact surface 11 may have other shapes, such as a rectangle, a square, an oval, a circle, and the like.

FIG. 2C is an exploded perspective view of the sensor 10. A first-axis (A-A') cross-section of the finger contact surface 11 may be convexly curved in an outward direction of the main body MB.

For example, the first-axis cross-section (A-A' cross-section) of the finger contact surface 11 may have a shape in which the height of the cross-section gradually decreases as the distance to the center of the finger contact surface 11 increases. For example, the first-axis cross-section of the finger contact surface 11 may have the same or similar shape to a portion of a circular or elliptical shape.

In another example, the first-axis cross-section of the finger contact surface 11 may have a shape in which the height of a given region of the cross-section from the center of an upper portion is horizontal and the height gradually decreases thereafter as the distance to the center increases. For example, the first-axis cross-section may have a shape in which the height gradually decreases in the form of a curve or in a straight line after a given point at a predetermined radius from the center of the upper portion. In this case, the finger contact surface 11 may be gradually lowered in a curved or straight line from the upper portion to a given point and be vertically lowered after the given point to a bottom portion, or may be continuously lowered in a curved or straight line from the upper portion to the bottom portion.

In another example, the first-axis cross-section of the finger contact surface 11 may be a plane. For example, the first-axis cross-section of the finger contact surface 11 is horizontal and the left and right ends may have a right angle.

The embodiment of the shape of the first-axis cross-section of the finger contact surface 11 may also be applied as an embodiment of the shape of the second-axis cross-section (B-B' cross-section). The first-axis cross-section and the second-axis cross-section may have the same shape or different shapes. When the finger contact surface 11 forms a curved surface, deeper deformation of a finger may be made when the finger is pressed with the same force, compared to the case of forming a flat surface. Therefore, it is possible for the user to produce the same deformation of the finger by applying less force to the finger contact surface 11.

Referring back to FIG. 2C, the finger contact surface 11 may include a first light transmissive region 12a formed on a part, a second light transmissive region 12b spaced apart from the first light transmissive region 12a and formed on another part thereof, and a third light transmissive region 12c formed between the first light transmissive region 12a and the second light transmissive region 12b. The remaining region of the finger contact surface 11 may be a light non-transmissive region. The first light transmissive region 12a, the second light transmissive region 12b, and the third light transmissive region 12c may each include holes formed in a circular, elliptical, or polygonal shape. In addition, each hole may be closed with a cover made of a transparent material, such as glass, plastic, or the like, to pass light therethrough. In this case, an individual cover may be configured to close each hole, or one cover integrally formed may be configured to cover all three holes. The first light transmissive region 12a, the second light transmissive region 12b, and the first light transmissive region 12c may be arranged on the first axis.

The light sensor 20 may be disposed inside the housing HS. However, the embodiment is not limited thereto, and the light sensor 20 may be disposed at a lower end outside the housing HS.

The light sensor 20 may include light sources 21a and 21b that irradiate a finger when the finger is placed on and in contact with the finger contact surface 11, and a photodetector 22 that detects light scattered or reflected by the tissue on the surface or inside of the finger that is irradiated by the light sources 21a and 21b.

The light sources 21a and 21b may include a first light source 21a and a second light source 21b disposed on both sides of a substrate of the light sensor 20 as illustrated. However, the number of light sources is not limited. In this case, the light sources 21a and 21b each may include at least one of a light emitting diode (LED), a laser diode, and a phosphor, but are not limited thereto.

The first light source 21a and the second light source 21b may be configured to emit light of different wavelengths from each other. For example, both of the first light source 21a and the second light source 21b may emit light of infrared (IR) wavelength or green wavelength. Alternatively, one of the first light source 21a and the second light source 21b may emit light of infrared wavelength and the other may emit light of green wavelength. In addition, each of the light sources 21a and 21b may include a plurality of LEDs and the plurality of LEDs may all be configured to emit light of the same wavelength or some of the plurality of LEDs may be configured to emit light of different wavelengths. For example, the light source 21a may include an IR LED emitting light of an infrared wavelength and a green LED emitting light of a green wavelength and the light source 21b may also include an IR LED and a green LED.

The photodetector 22 may be interposed between the first light source 21a and the second light source 21b on the substrate of the light sensor 20. The photodetector 22 may be a complementary metal-oxide semiconductor (CMOS) image sensor, but is not limited thereto, such that the photodetector 22 may include a photodiode, a phototransistor (PTr), a charge-coupled device (CCD) image sensor, and the like. When the light scattered or reflected by the finger is detected, the photodetector 22 may convert the intensity of the light into electrical digital light signal data and transmit the digital light signal data to a processor.

In addition, the force sensor 30 may be disposed inside of the housing HS or at the bottom outside of the housing HS. The force sensor 30 may be laminated on the bottom or the top of the light sensor 20. The force sensor 30 may measure a pressing force of a finger in contact with the finger contact surface 11. For example, the force sensor 30 may include a strain gauge, and measure the magnitude of force at which the user presses the sensor 10.

Figure 3:
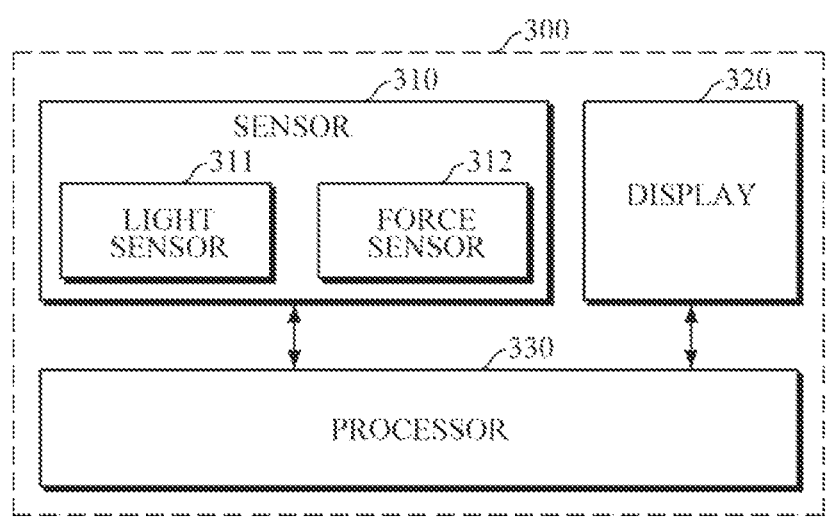
FIG. 3 is a block diagram illustrating a wearable device according to an embodiment.

FIG. 3 is a block diagram illustrating a wearable device according to one embodiment.

Referring to FIG. 3, the wearable device 300 includes a sensor 310, a display 320, and a processor 330.

The sensor 310 may include a light sensor 311 and a force sensor 312.

The light sensor 311 may include at least one light source that emits light to a finger when the finger touches a finger contact surface, and a photodetector that detects light scattered or reflected by the surface and/or the internal tissue of the finger irradiated by the light source.

When the user touches the sensor 310 with the finger, the light sensor 311 may acquire a partial fingerprint image of a region of the finger (hereinafter referred to as a "current measurement site of the finger") in current contact with the sensor 310.

In addition, the light sensor 311 may acquire a pulse wave signal for a predetermined period of time when the user's finger is in contact with the sensor 310. The acquired pulse wave signal may be processed by the processor 330 for the purpose of bio-information estimation and other various operations.

The force sensor 312 may measure a force exerted on the sensor 310 when the pressing force is increased or decreased while the user's finger is in contact with the finger contact surface.

The display 320 may output a processing result of the processor 330 to visually provide information to the user. The display 320 may include a touch screen for touch input and include an on-screen fingerprint sensor for recognition of a fingerprint from the user's finger.

When the partial fingerprint image is acquired from the current measurement site of the finger by the light sensor 311, the processor 330 may guide the user through the display 320 so that an optimal (or improved) measurement site is brought in contact with the sensor 310 by using the acquired partial fingerprint image and a full fingerprint image acquired in advance from the same finger of the user. In this case, the optimal measurement site of the finger may mean a specific region of the finger at which an optimal (or improved) pulse wave signal is acquired when the specific region is in contact with the sensor 310, and may be a common measurement site predetermined for a plurality of users or a personalized measurement site predetermined for each user.

When the optimal measurement site of the finger is in contact with the sensor 310 according to the guidance for the measurement site of the finger and the pulse wave signal is acquired, the processor 330 may estimate bio-information using the acquired pulse wave signal. In this case, the bio-information may include one or more of a blood pressure, a vascular age, an arterial stiffness, an aortic artery pressure waveform, a vascular elasticity, a stress index, and a fatigue level, but is not limited thereto. Also, the processor 330 may perform various functions, such as fingerprint authentication, in addition to the bio-information estimation. When fingerprint authentication is successful for a predefined user, the processor 330 may allow the user to perform a desired operation, such as execution of a specific application, through the sensor 310.

The processor 330 may acquire the full fingerprint image from the user's finger in advance or predetermine an optimal measurement site of the user's finger in advance.

In addition, the processor 330 may determine whether the optimal measurement site of the finger is in contact with the sensor 310, and when the optimal measurement site of the finger is in contact with the sensor 310, the processor 330 may control the sensor 310 to acquire a pulse wave signal. In this case, the processor 330 may guide a contact pressure through the display 320 such that the user adjusts the force of the finger pressing the sensor 310 in order to acquire an oscillometric pulse wave.

Hereinafter, a series of processes for estimating bio-information will be described with reference to FIGS. 4 to 7B.

FIG. 4 illustrates an embodiment in which the wearable device 300 guides a finger measurement site.

(1) of FIG. 4 is a diagram for describing a process of acquiring a full fingerprint image of a finger for each user. The process of acquiring the full fingerprint image of a user's finger may be performed at the time of registering a user in the wearable device 300. Alternatively, this process may be performed at the time of calibration, at predefined intervals, or upon request of a user. The acquisition of the full fingerprint image 420 may be performed on a finger from which a pulse wave signal is to be measured, and full fingerprint images of multiple fingers for each user may be acquired.

Referring to (1) of FIG. 4, when a finger 410 is in contact with the display 320, the wearable device 300 may acquire the full fingerprint image 420 of the contacting finger 410 through an on-screen fingerprint sensor mounted in the display 320.

Figure 5A:
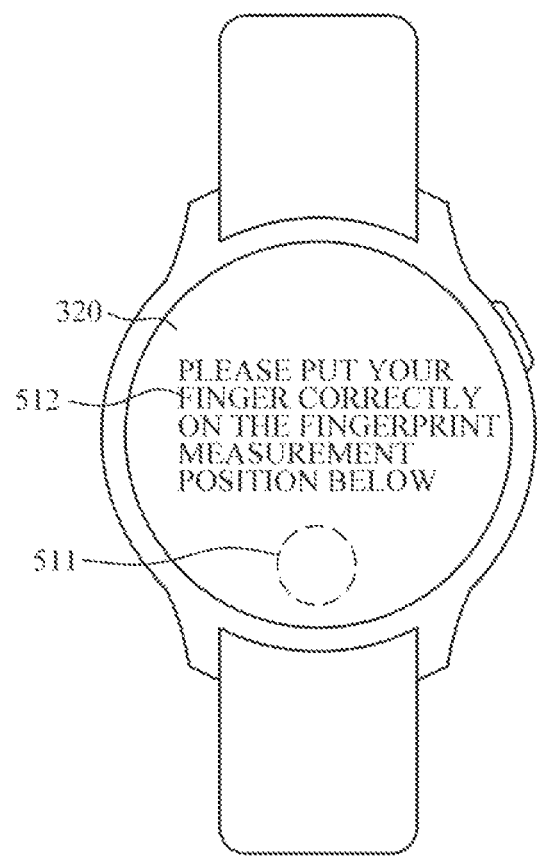
FIGS. 5A to 5C are diagrams illustrating an embodiment of acquiring a full fingerprint image of a finger.
Figure 5B:
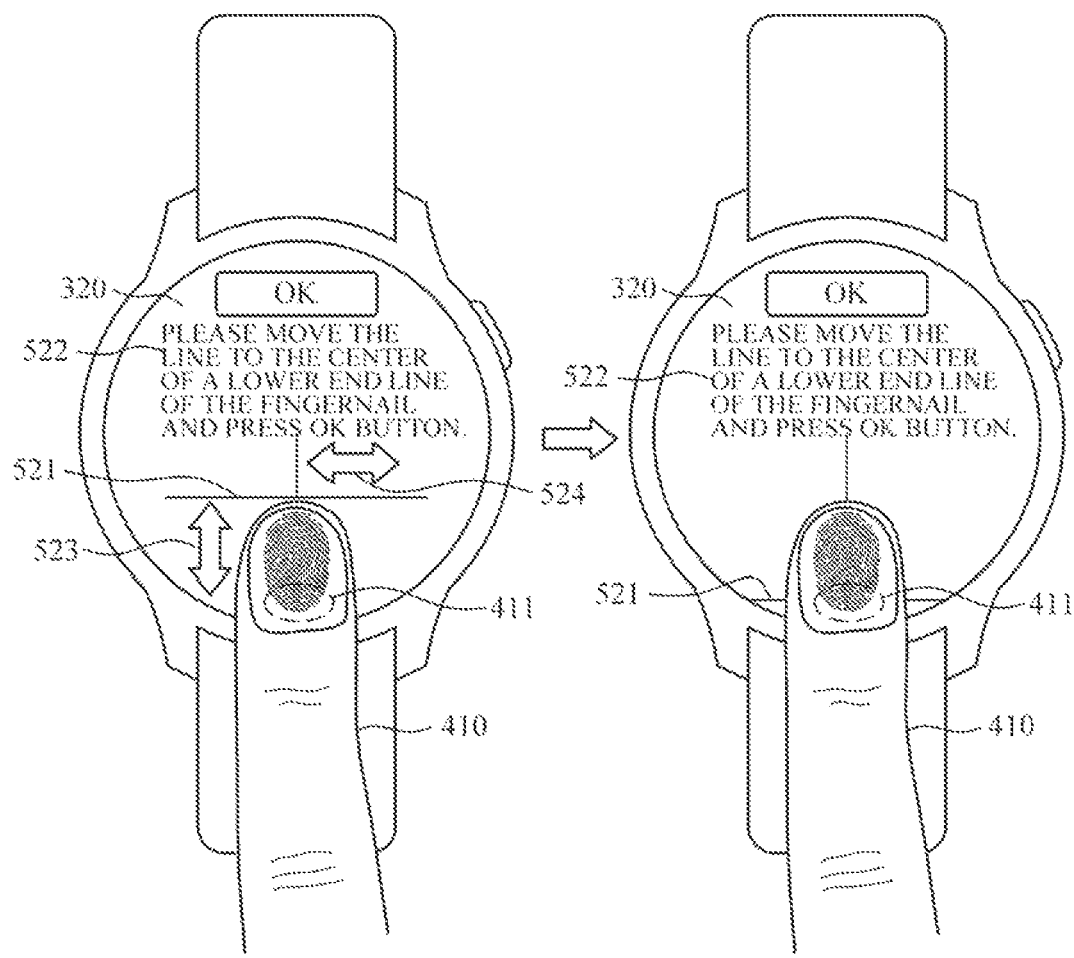
Figure 5C:
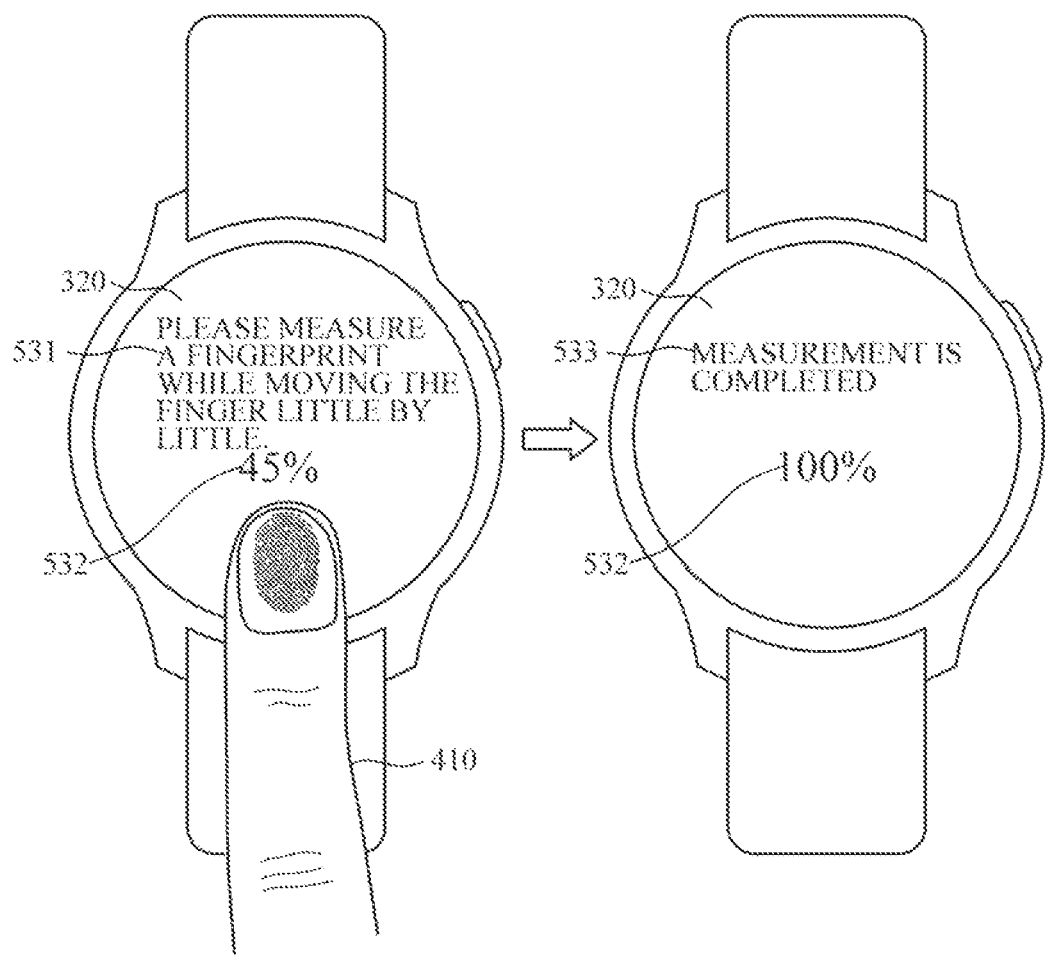

FIGS. 5A to 5C illustrate embodiments in which the wearable device acquires a full fingerprint image of a finger.

Referring to FIG. 5A, the processor 330 may display a marker 511 indicating a region of a fingerprint sensor on the display 320. In this case, text 512, such as "please put your finger correctly on the fingerprint measurement position below" may be further displayed to allow the user to bring a finger into contact with the position of the marker 511 indicating the region of the fingerprint sensor.

Referring to the left drawing of FIG. 5B, when the user puts the finger 410 on the position of the marker 511 indicating the region of the fingerprint sensor, the processor 330 may display a marker 521 on the display 320 to specify a contact direction of the finger 410 and a reference measurement site. In this case, the reference measurement site of the fingerprint 410 may mean a fingerprint central point or a central portion under a fingernail. The marker 521 may be in the shape of "T" as illustrated. However, the shape of marker 521 is not particularly limited. In addition, the processor 330 may display an up and down arrow 523 and/or a left and right arrow 524 around the marker 521 to move the marker 521 for specifying the reference measurement site up and down and left and right. In addition, the processor 330 may display text 522, such as "please move the line to the center of a lower end line of the fingernail and press OK button," on the display 320 so that the user moves the marker 521 and specifies the reference measurement site and the contact direction.

When the user moves the marker 521 to match a lower end line of the marker 521 to a display position 411 of the fingernail and matches a line perpendicular to the lower end line of the marker 421 to the contact direction of the finger as shown in the right drawing of FIG. 5B, the processor 330 may display text 531, such as "please measure a fingerprint while moving the finger little by little," as shown in FIG. 5C, so that the fingerprint can be evenly acquired from the entire finger 410. In this case, text indicating a degree at which the full fingerprint image of the finger 410 is acquired may be further displayed. When the full fingerprint image is acquired, the processor 330 may display text 533, such as "measurement is completed," to notify that the acquisition of full fingerprint image is completed.

Referring back to FIG. 4, (2) is a diagram for describing a process of determining an optimal measurement site of a finger for each user and determining whether the determined optimal measurement site is in contact with the sensor. In this case, the process of determining the optimal measurement site of the finger may be performed at the time of registering a user in the wearable device 300, at predefined intervals, or upon request of a user. In addition, the process of determining whether the optimal measurement site is in contact with the sensor may be performed at the time of estimating bio-information.

Referring to (2) of FIG. 4, the processor 410 may display the acquired full fingerprint image 420 of the finger 410 on the display 320 and display and superimpose the marker 431 indicating the optimal measurement site of the finger 410 over the full fingerprint image 420 so that the user can bring the optimal measurement site of the finger 410 into contact with the sensor 310.

When the user brings the finger 410 into contact with the sensor 310 according to the marker 431 indicating the optimal measurement site, the sensor 310 may acquire a partial fingerprint image of the current measurement site of the finger 410.

The processor 330 may compare the full fingerprint image 420 with the partial fingerprint image of the current measurement site to determine whether the current measurement site matches the optimal measurement site. After the partial fingerprint image of the current measurement site is acquired by the sensor 310, or when the determination result indicates that the current measurement site does not match the optimal measurement site, the processor 330 may display and superimpose the marker 432 indicating the current measurement site of the finger 431 over the full fingerprint image 420.

Figure 6B:
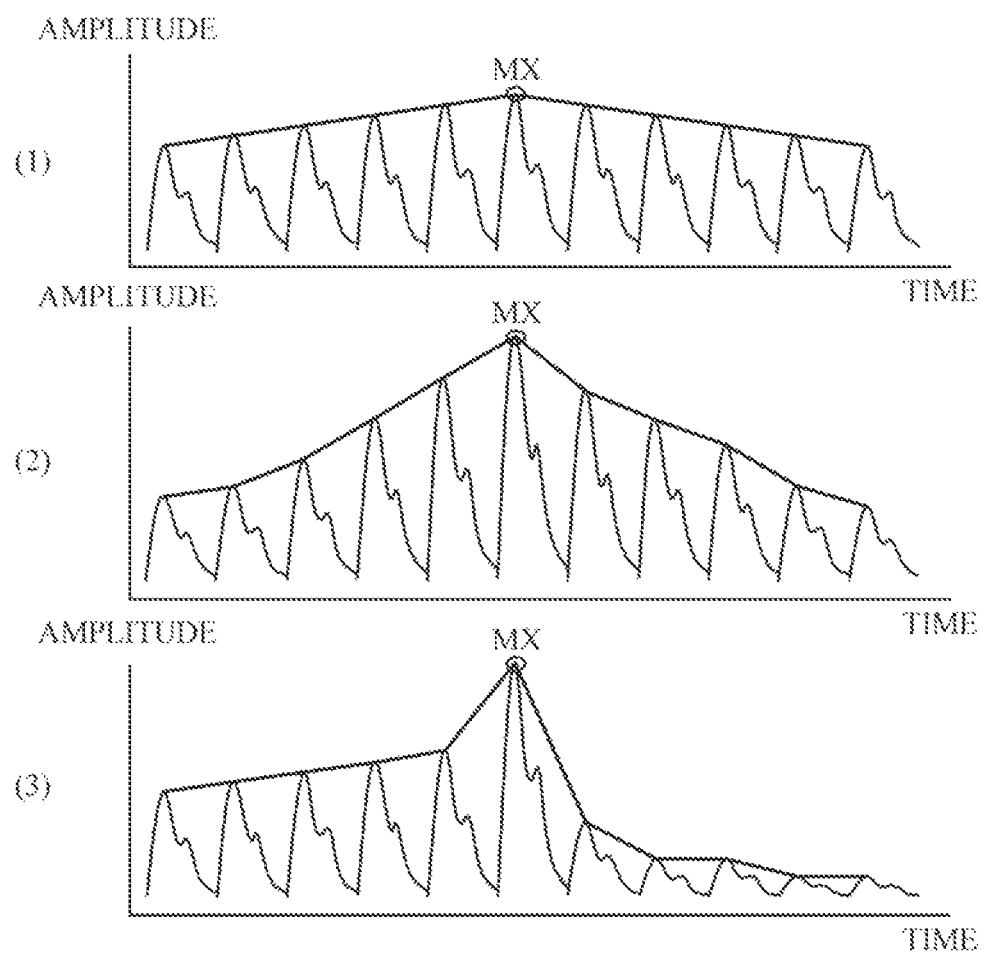
Figure 6C:
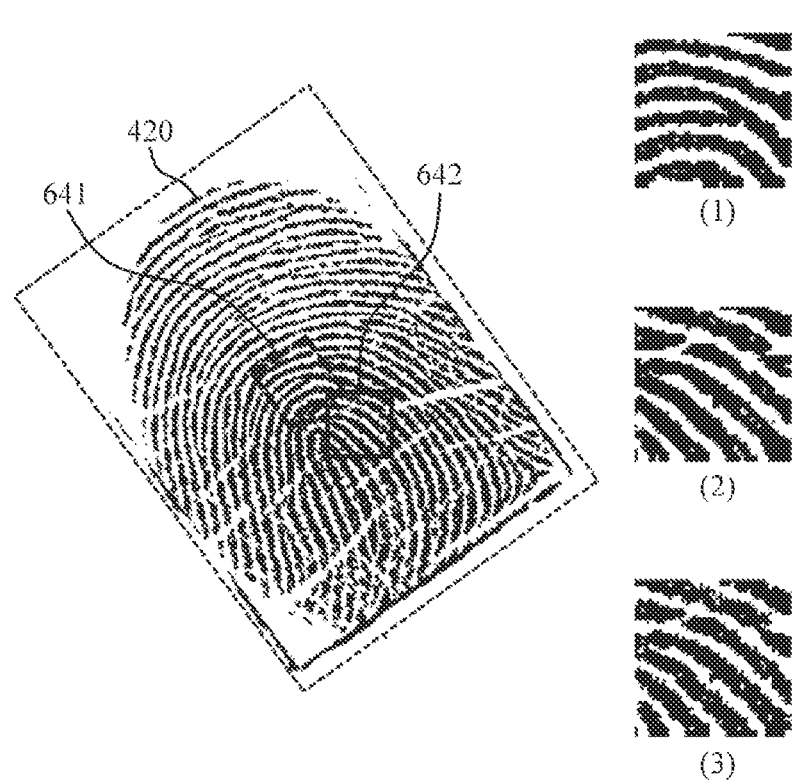

FIGS. 6A to 6C are diagrams illustrating an embodiment of determining and guiding an optimal measurement site of a finger.

Referring to FIG. 6A, the processor 330 may acquire pulse wave signals from a plurality of target measurement sites of a finger 410 for each user and determine an optimal measurement site of the finger 410 on the basis of the pulse wave signal at each target measurement site. For example, as shown in (1) of FIG. 6A, the processor 330 may display a full fingerprint image 420 on the display 310 and display a marker 611 indicating a first target measurement site over the full fingerprint image 420. When the user checks the first target measurement site and touches the sensor 310 with the finger 410, the sensor 310 may acquire a first pulse wave signal from the finger 410. In this case, the processor 330 may display a marker 612 indicating a current measurement site of the contacting finger 410 on the full fingerprint image 420.

Then, as shown in (2) of FIG. 6A, the processor 330 may display a second marker 621 indicating a second target site on the full fingerprint image 420, and when the finger 410 accordingly comes into contact with the sensor 310, the sensor 310 may acquire a second pulse wave signal. In this case, the processor 330 may display a marker 622 indicating a current measurement site of the finger 410 on the full fingerprint image 420. Similarly, as shown in (3) of FIG. 6A, the processor 330 may display a marker 631 indicating a third target site on the full fingerprint image 420, and when the finger 410 accordingly comes into contact with the sensor 310, the sensor 310 may acquire a third pulse wave signal. In this case, the processor 330 may display a marker 632 indicating a current measurement site of the finger 410 on the full fingerprint image 420.

FIG. 6B illustrates a pulse wave signal acquired from each target measurement site of the finger 410 of the user. The processor 330 may determine an optimal measurement site using the pulse wave signals 1, 2, and 3 acquired from a plurality of target measurement sites. For example, assuming that the second pulse wave signal 2 in FIG. 6B is an optimal pulse wave signal, the second target measurement site from which the second pulse wave signal 2 may be determined to be the optimal measurement site.

The processor 330 may compare a waveform of each pulse wave signal 1, 2, and 3 with a waveform of a previously acquired reference pulse wave signal and determine that a target measurement site from which the most similar pulse wave signal is acquired is the optimal measurement site. In this case, the reference pulse wave signal may be a pulse wave signal acquired from a finger of a user using a more accurate pulse wave signal measurement device, or pulse wave signals acquired from a plurality of users. In another example, a feature point of each pulse wave signal 1, 2, and 3, for example, a maximum point MX of amplitude, may be extracted, and the determination may be made by comparing a predetermined threshold with a difference between an extracted maximum amplitude value and the amplitude of a base point, or a difference between the maximum amplitude value and the amplitude at a point immediately before or after the maximum point MX, comparing a maximum slope with a predetermined threshold, and the like. However, examples, determination criteria, or the like, of the extracted feature point are not particularly limited to the examples disclosed herein, and may be variously defined for each user through preprocessing.

FIG. 6C is a diagram for describing a process of determining whether the optimal measurement site of the finger 410 is in contact with the sensor. (1) of FIG. 6C illustrates a partial fingerprint of the optimal measurement site, that is, a fingerprint at a position where a marker 641 indicating the optimal measurement site of the full fingerprint image 420 is located. (2) of FIG. 6C illustrates a partial fingerprint at a current measurement site of the finger, that is, an actual partial fingerprint at a finger contact position of the finger in contact with the sensor. (3) of FIG. 6C illustrates a partial fingerprint similar to the partial fingerprint of the current measurement site, which is found in the full fingerprint image 420, that is, a fingerprint at a position where a marker 642 indicating the current measurement site in the full fingerprint image 420 in the left is located.

When the user brings the finger into contact with the sensor 310 by referring to the full fingerprint image 420 displayed on the display 320 and a marker 641 indicating the optimal measurement site on the full fingerprint image, the sensor 410 may acquire a partial fingerprint image 2 of the current measurement site of the finger.

The processor 330 may search for a site having a fingerprint shape similar to the partial fingerprint image of the current measurement site acquired by the sensor 310 from the full fingerprint image 420 through fingerprint pattern analysis. The processor 330 may compare the partial fingerprint of the found site and the partial fingerprint of the optimal measurement site and determine whether the current measurement site matches the optimal measurement site, that is, whether the optimal measurement site of the finger is in contact with the sensor 310. In this case, whether the current measurement site matches the optimal measurement site may be determined not only when they completely match each other, but it may be determined that they match each other when a predetermined criterion is satisfied. For example, when the similarity between the partial fingerprint of the current measurement site and the partial fingerprint pattern of the optimal measurement site is greater than or equal to a threshold and/or when a degree at which a region of the marker 641 at the optimal measurement site overlaps a region of the marker 642 at the current measurement site is greater than or equal to a predetermined threshold, it may be determined that the current measurement site matches the optimal measurement site. However, a criterion for determining whether the current measurement site matches the optimal measurement site may be variously defined.

Immediately after a site having a fingerprint shape similar to the partial fingerprint image of the current measurement site is found or when it is determined that the current measurement site and the optimal measurement site do not match, the processor 330 may display a marker 642 indicating the current measurement site on the full fingerprint image 420 to guide the user to move the finger position to the optimal measurement site.

Referring back to (3) of FIG. 4, when it is determined that the optimal measurement site of the finger 410 is in contact with the sensor 310, a change in contact pressure between the finger 410 and the sensor 310 may be guided for a predetermined period of time in order to acquire an oscillometric pulse wave signal from the finger 410. For example, the processor 330 may display a marker 441 indicating an upper limit of a reference contact pressure to be applied to the sensor 310 by the finger 410 and a marker 442 indicating a lower limit on the display 320 as illustrated. Accordingly, when the finger 410 of the user applies a force to the sensor 310, the light sensor 311 of the sensor 310 may acquire a pulse wave signal, and the force sensor 312 of the sensor 310 may measure a contact force applied by the finger 410 to the sensor 310. The processor 330 may acquire a contact pressure on the basis of the contact force and display a marker 443 indicating the acquired actual contact pressure on the display 320.

When the pulse wave signal and the contact force are measured at the optimum measurement site of the finger as described above, the processor 330 may estimate bio-information based on the measured pulse wave signal and the contact force. For example, the processor 330 may convert the contact force to the contact pressure based on the area of the finger contact surface of the sensor 330, and estimate blood pressure on the basis of the oscillometry, based on the pulse wave signal and the contact pressure.

Figure 7A:
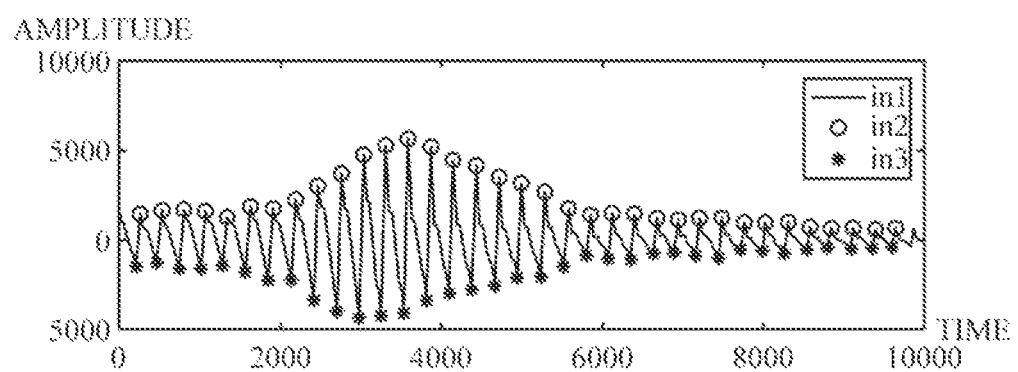
FIGS. 7A and 7B are diagrams for describing oscillometry-based blood pressure measurement.
Figure 7B:
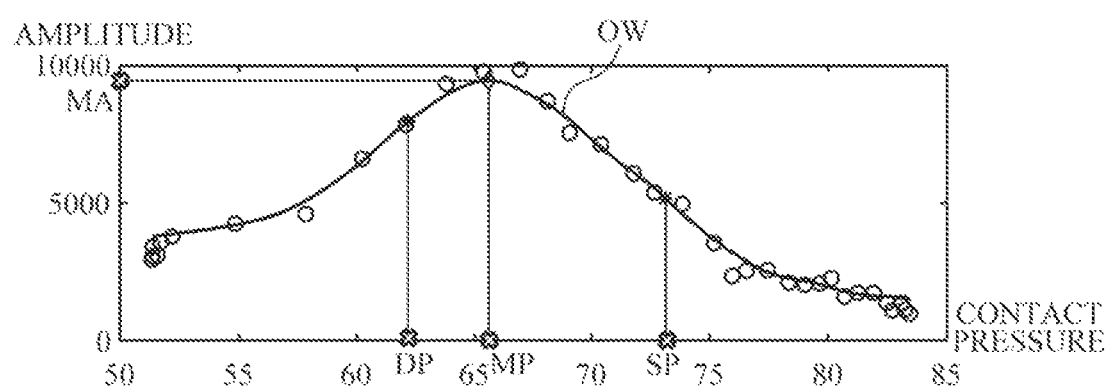

FIGS. 7A and 7B are diagrams for describing oscillometry-based blood pressure measurement.

FIG. 7A illustrates a pulse wave signal measured while gradually increasing force in a state a user's finger is in contact with a finger contact surface. FIG. 7B is an oscillometric envelope (OW) graph showing a relationship between amplitude of an oscillometric pulse wave signal and a contact pressure. For example, the processor 330 may extract a peak-to-leak point by subtracting an amplitude value in3 of a minus (−) point from an amplitude value in2 of a plus (+) point of a pulse wave signal waveform envelope in1 at each measurement time point and acquire an oscillometric envelope OW by plotting amplitudes of the peak-to-peak points of each measurement time point on the basis of the contact pressure at the corresponding time point.

The processor 330 may extract a feature point from the acquired oscillometric envelope OW and estimate blood pressure using the acquired feature point. For example, mean blood pressure may be determined based on a contact pressure value MP at the maximum peak point in the oscillometric envelope OW. In addition, diastolic blood pressure may be determined based on a contact pressure DP at a point at which an amplitude has a value equal to a first percentage (e.g., 0.5 to 0.7) of the maximum amplitude value MA in the left of the maximum peak point, and systolic blood pressure may be determined based on a contact pressure SP at a point at which an amplitude has a value equal to a second percentage (e.g., 0.5 to 0.7) of the maximum amplitude value MA in the right of the maximum peak point. For example, the contact pressure values MP, DP, and SP may be determined as mean blood pressure, diastolic blood pressure, and systolic blood pressure, respectively, and in another example, mean blood pressure, diastolic blood pressure, and systolic blood pressure may be estimated using a blood pressure estimation model that defines the relationship between each contact pressure value MP, DP, and SP and blood pressure.

Referring back to FIG. 3, when bio-information is estimated, the processor 330 may provide a bio-information estimation value to the user by displaying the bio-information estimation value on the display 320. The processor 330 may divide the display 320 into two or more sections, output information, such as the pulse wave signal, the contact pressure, and the like, used in estimation of the bio-information in a first section in a graph form, and output the bio-information estimation value, warning information, and the like, to a second section.

Figure 8:
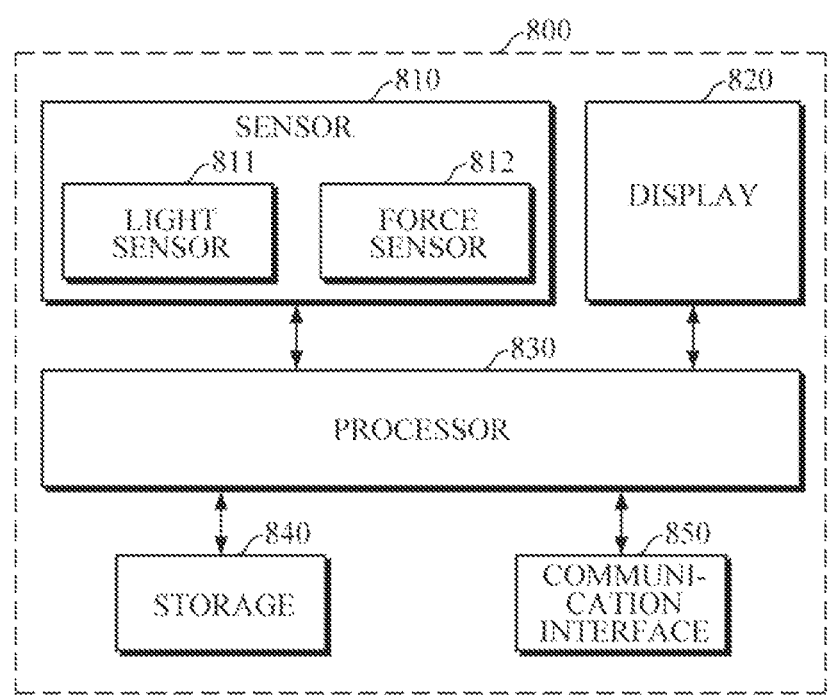
FIG. 8 is a block diagram illustrating a wearable device according to another embodiment.
Figure 9B:
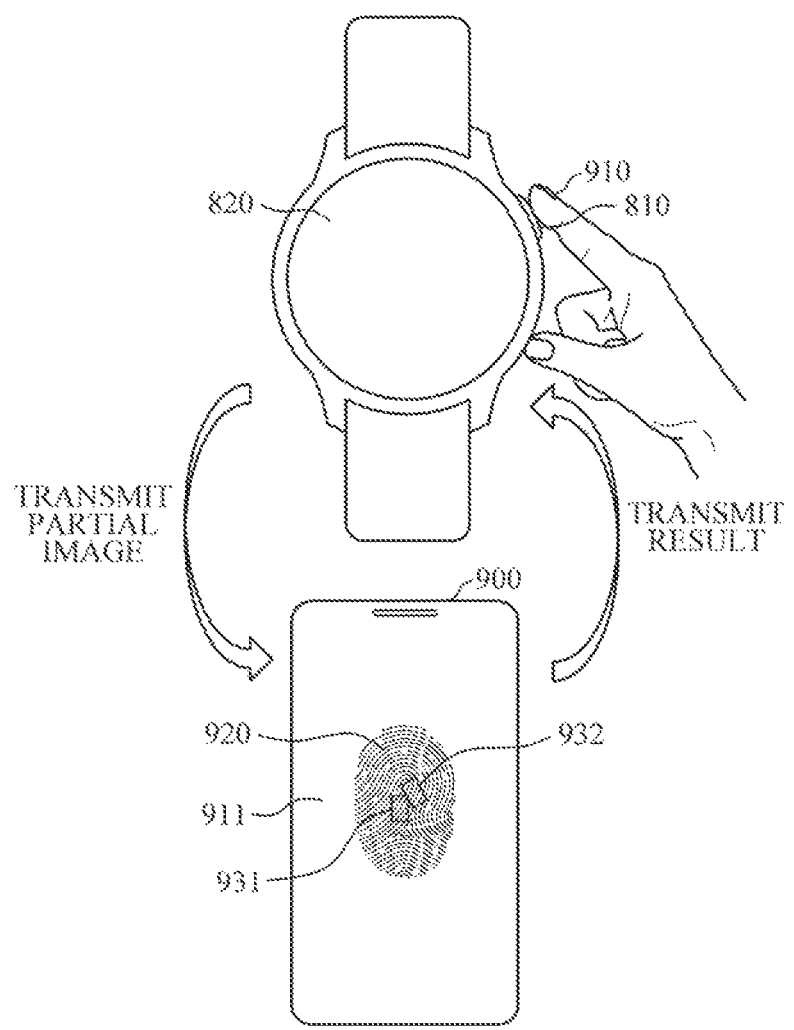

FIG. 8 is a block diagram illustrating a wearable device according to one embodiment. FIGS. 9A and 9B are diagrams illustrating another embodiment of determining an optimal measurement site of a finger.

Referring to FIG. 8, the wearable device 800 may include a sensor 810, a display 820, a processor 830, a storage 840, and a communication interface 850. The sensor 810, the display 820, and the processor 830 are described above with reference to FIG. 3, and hence will be briefly described below.

The sensor 810 may include a light sensor 811 and a force sensor 812. The light sensor 811 may acquire a partial fingerprint image of a finger and a pulse wave signal when the finger comes into contact with the sensor 810. The force sensor 812 may measure a contact force acting between the finger and the sensor 810.

The processor 830 may estimate bio-information using the pulse wave signal and the contact force acquired through the sensor 810.

The storage 840 may store information, such as the pulse wave signal, partial fingerprint image, and contact force measured by the sensor 840. In addition, when the bio-information is estimated by the processor 830, the storage 840 may store a bio-information estimation result. Also, the storage 840 may store basic information required for estimating bio-information, for example, user information, such as a user's age, sex, health status, and the like, the bio-information estimation model, the reference contact pressure, the full fingerprint image, an optimal measurement image of a finger, and the like.

In this case, the storage 840 may include at least one type of storage medium of a flash memory type, a hard disk type, a multimedia card micro type, a card type memory (for example, secure digital (SD) or extreme digital (XD) memory), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk, but is not limited thereto.

The communication interface 850 may communicate with an external device using a communication technology and transmit and receive various types of data. For example, the communication interface 850 may transmit a bio-information estimation result to the external device. In addition, the communication interface 850 may receive basic information required for estimating bio-information from the external device. In this case, the external device may include an information processing device, such as a smartphone, a tablet PC, a desktop PC, a notebook PC, and the like. In this case, the communication technology may include Bluetooth communication, Bluetooth low energy (BLE) communication, near field communication unit, wireless local access network (WLAN) communication, ZigBee communication, infrared data association (IrDA) communication, wireless fidelity Wi-Fi direct (WFD) communication, ultra wideband (UWB) communication, Ant+ communication, Wi-Fi communication, and 3G, 4G, and 5G communication technologies. However, the communication technology is not limited thereto.

The processor 830 may provide guidance related to a finger measurement site and/or the bio-information estimation result to the user through the display 820. In addition, the processor 830 may perform operations of acquiring a full fingerprint image of a finger, determining an optimal measurement site of the finger, and determining whether the optimal measurement site is in contact with the sensor 810, in cooperation with the external device through the communication interface 850 when necessary, such as when the display 820 does not include an on-screen fingerprint sensor, when computing performance of the wearable device 800 is relatively low, or when there is a user's request.

In one example, referring to (1) of FIG. 9A, a full fingerprint image of a finger 910 may be acquired through a smartphone 900 of a user. For example, the processor 830 may receive the full fingerprint image from the smartphone 900 through the communication interface 850 at the time of registering the user. When there is a request from the wearable device 800 or when the user directly requests the smartphone 900, the smartphone 900 may acquire the full fingerprint image of the finger in the same manner as shown in FIGS. 5A to 5C using a display 911 of the smartphone 900 and transmit the acquired full fingerprint image to the wearable device 800.

Referring to (2) and (3) of FIG. 9A, the processor 830 may display the full fingerprint image 920, a marker 931 indicating an optimal measurement site, and a marker 932 indicating a current measurement site of the finger 910 on the display 820 as described with reference to (2) and (3) of FIG. 4, and when it is determined that the optimal measurement site of the finger 910 is in contact with the sensor 810, the processor 830 may display markers 941, 942, and 943 for guiding a contact pressure on the display 820.

In another example, referring to FIG. 9B, the process of (2) of FIG. 9A may be performed in association with the smartphone 900 as illustrated. For example, the processor 830 may request the smartphone 900 through the communication interface 850 to display the full fingerprint image 920 and the marker 931 indicating the optimal measurement site on the display 911.

In addition, when the user brings the finger into contact with the sensor 810 by referring to the optimal measurement site displayed on the smartphone 900, the communication interface 850 transmits the partial fingerprint image of the current measurement site acquired through the sensor 810 to the smartphone 900. When the partial fingerprint image of the current measurement site is received from the communication interface 850, the smartphone 900 may compare the partial fingerprint of the optimal measurement site with the partial fingerprint of the current measurement site to determine whether they match each other as described above. When it is determined that they do not match, the smartphone 900 may display a marker 932 indicating the current measurement site, and the above processes may be repeated when the user brings the finger into contact with the sensor 810 again by adjusting the measurement site of the finger.

The processor 830 may receive a result of determining whether the current measurement site of the finger and the optimal measurement site match each other, and if they match, may perform the process (3) of FIG. 9B.

Figure 10:
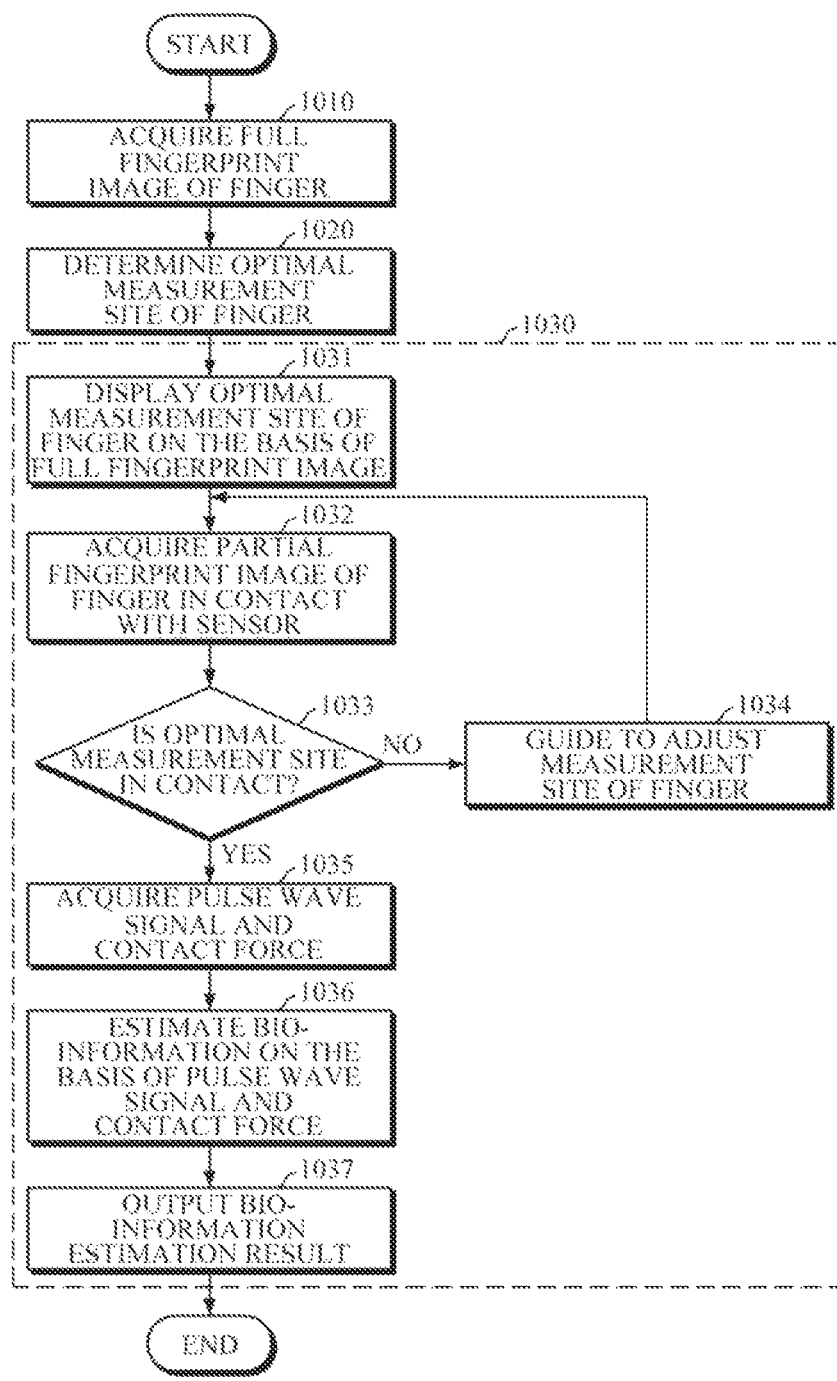
FIG. 10 is a flowchart illustrating a method of estimating bio-information according to an embodiment.

FIG. 10 is a flowchart illustrating a method of estimating bio-information according to an embodiment.

The method of FIG. 10 is performed by the wearable device according to the embodiment of FIG. 3 and has been described above, and thus will be briefly described below.

First, the wearable device 300 acquires a full fingerprint image of a finger (operation 1010). Full fingerprint images may be acquired from a plurality of fingers for each user. The wearable device 300 may visually provide the user with guide information for acquiring a full fingerprint image.

Then, an optimal measurement site of a finger may be determined (operation 1020). Pulse wave signals may be measured at a plurality of target measurement sites and a target measurement site at which an optimal pulse wave signal is acquired may be determined as the optimal measurement site.

Then, according to a request for estimating bio-information, the optimal measurement site of the finger may be guided to be in contact with the sensor and bio-information may be estimated using the pulse wave signal acquired at the optimal measurement site and the force sensor (operation 1030).

For example, the optimal measurement site of the finger may be displayed on the basis of the full fingerprint image acquired in operation 1010 (operation 1031). Then, a partial fingerprint image of the finger in contact with the sensor may be acquired (operation 1032).

Then, it may be determined whether the optimal measurement site of the finger is in contact with the sensor on the basis of the acquired partial fingerprint image of the finger (operation 1033). As described above, the acquired partial fingerprint image and a fingerprint image corresponding to the optimal measurement site in the full fingerprint image may be compared to determine whether they match each other.

When a result of determination 1033 indicates that the optimal measurement site of the finger is not in contact with the sensor (operation 1033—NO), a marker indicating the current measurement site or a marker indicating the direction in which the finger should move may be displayed to guide the user to adjust the measurement site of the finger (operation 1034).

When the result of determination 1033 indicates that the optimal measurement site of the finger is in contact with the sensor (operation 1033—YES), a pulse wave signal and a contact force may be acquired from the optimal measurement site of the finger (operation 1035). In this case, the wearable device may guide the contact pressure between the finger of the user and the sensor.

Then, bio-information may be estimated based on the pulse wave signal and the contact force (operation 1036) and a bio-information estimation result may be output (operation 1037). For example, contact pressure may be acquired based on the contact force, and blood pressure may be estimated based on oscillometry using the contact pressure and the pulse wave signal.

Figure 11:
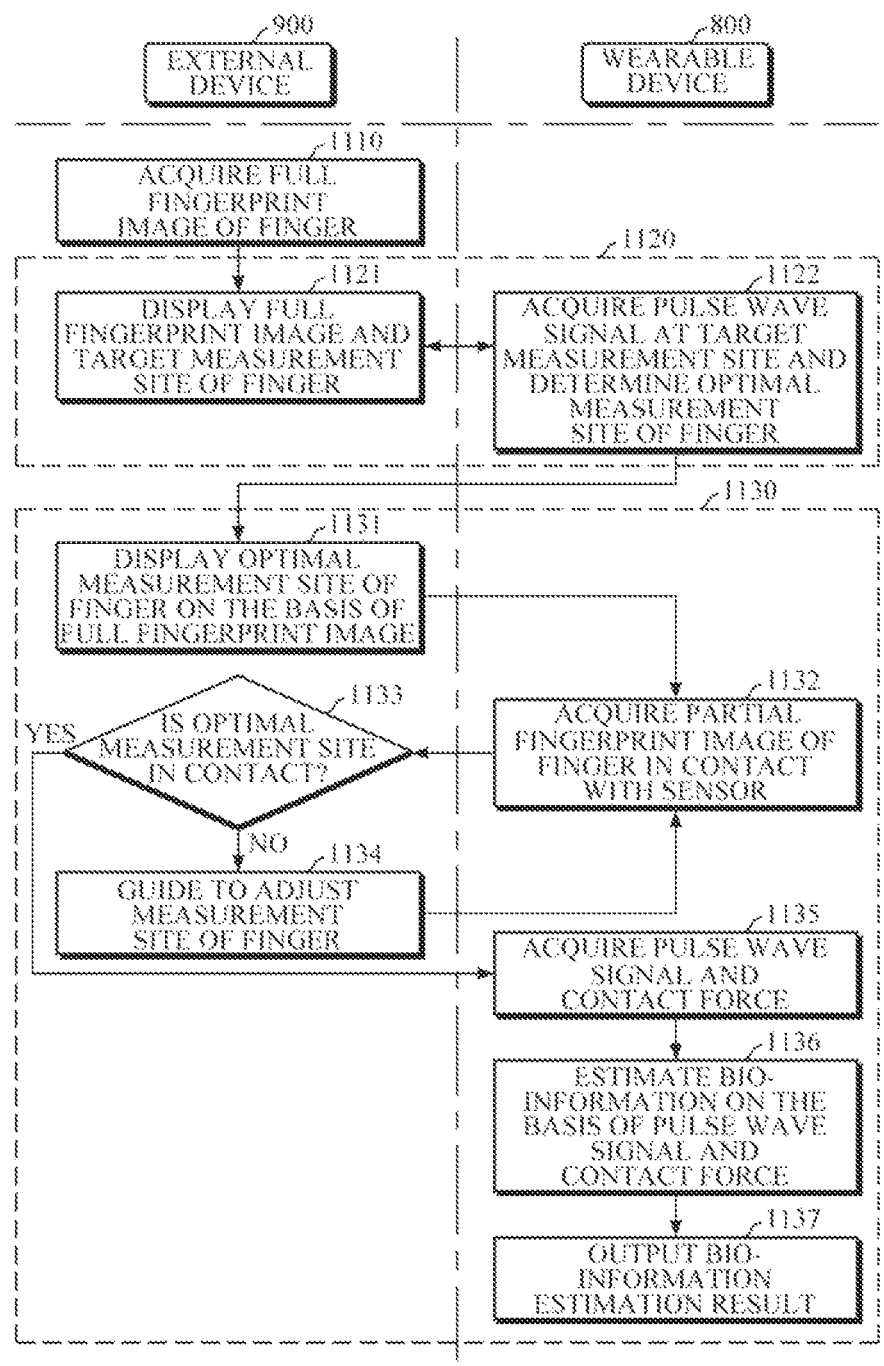
FIG. 11 is a flowchart illustrating a method of estimating bio-information according to another embodiment.

FIG. 11 is a flowchart illustrating a method of estimating bio-information according to another embodiment.

The method of FIG. 11 may be performed by the collaboration of the wearable device 800 and the external device 900 as described with reference to FIG. 8.

First, the external device 900 may acquire a full fingerprint image of a finger upon request of a user or the wearable device 800 (operation 1110).

Then, the external device 900 may display the full fingerprint image and a target measurement site of the finger upon request of the user or the wearable device 800 (operation 1121), and the wearable device 800 may acquire a pulse wave signal corresponding to each target measurement site when the finger is in contact with the sensor according to the guidance of the wearable device 800 for each target measurement site and determine an optimal measurement site of the finger (operation 1122).

Then, when a request for measuring bio-information is received, the wearable device 800 may guide the measurement site of the finger and estimate the bio-information in cooperation with the external device 900 (operation 1130).

For example, when the request for measuring bio-information is received, the wearable device 800 may request the external device 900 to guide the measurement site of the finger, and the external device 900 may display the full fingerprint image and the optimal measurement site of the finger according to the request (operation 1131).

Then, the wearable device 800 may acquire a partial fingerprint image of the finger through the sensor (operation 1132), and transmit the acquired partial fingerprint image to the external device 900.

Then, the external device 900 may compare the partial fingerprint image of the current measurement site of the finger received from the wearable device 800 with the fingerprint of the optimal measurement site to determine whether the optimal measurement site of the finger is in contact with the sensor (operation 1133). When it is determined that the optimal measurement site of the finger is not in contact with the sensor (operation 1133—NO), the external device 900 may guide the user to adjust the measurement site (1134). When it is determined that the optimal measurement site of the finger is in contact with the sensor (operation 1133—YES), the external device 900 may transmit a determination result to the wearable device 800.

Then, the wearable device 800 may acquire a pulse wave signal and a contact force from the optimal measurement site of the finger (operation 1135), estimate bio-information based on the pulse wave signal and the contact force (operation 1136), and output and provide a bio-information estimation result to the user (operation 1137).

The current embodiments can be implemented as computer readable code in a non-transitory computer readable recording medium. Code and code segments constituting the computer program can be inferred by a skilled computer programmer in the art. The computer readable recording medium includes all types of record media in which computer readable data are stored. Examples of the computer readable recording medium include a ROM, a RAM, a CD-ROM, a magnetic tape, a floppy disk, and an optical data storage. Further, the recording medium may be implemented in the form of a carrier wave such as Internet transmission. In addition, the computer readable recording medium may be distributed to computer systems over a network, in which computer readable codes may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A wearable device comprising:
   a main body;
   a processor configured to acquire a full fingerprint image of a finger of a user based on the finger being in contact with a display of the wearable device; and
   a sensor formed on a stem disposed on a side of the main body, and configured to acquire a partial fingerprint image of the finger of the user based on the finger being in contact with the sensor, wherein the processor is further configured to control the display to guide the user, based on the partial fingerprint image acquired from the sensor and the full fingerprint image of the finger acquired from the display, to permit a measurement site of the finger to contact the sensor.

2. The wearable device of claim 1, wherein the sensor comprises a finger contact surface configured to contact the finger, a light sensor configured to emit light to the finger in contact with the finger contact surface and detect light scattered or reflected from the finger, and a force sensor configured to measure a contact force between the finger and the finger contact surface.

3. The wearable device of claim 1, further comprising the display disposed on a surface of the main body,
wherein the processor is further configured to control the display to display the full fingerprint image of the finger, and display a marker indicating the measurement site of the finger on the displayed full fingerprint image.

4. The wearable device of claim 3, wherein the processor is further configured to:
determine whether the measurement site of the finger is in contact with the sensor based on the full fingerprint image and the partial fingerprint image; and
based on determining that the measurement site of the finger is not in contact with the sensor, control the display to display the marker indicating a current measurement site of the finger on the full fingerprint image displayed.

5. The wearable device of claim 4, wherein the processor is further configured to:
determine a site matching the partial fingerprint image from the full fingerprint image; and
compare a fingerprint image of the determined site with a fingerprint at a position where the marker indicating the measurement site is located to determine whether the measurement site of the finger is in contact with the sensor.

6. The wearable device of claim 4, wherein the processor is further configured to:
control the display to guide a contact pressure between the finger and the sensor based on determining that the measurement site of the finger is in contact with the sensor.

7. The wearable device of claim 1, further comprising the display disposed on a surface of the main body,
wherein the display comprises a fingerprint sensor, and
wherein the processor is further configured to acquire the full fingerprint image of the finger using the fingerprint sensor of the display.

8. The wearable device of claim 7, wherein the processor is further configured to:
control the display to display a first marker indicating a region of the fingerprint sensor on the display to permit the user to bring the finger into contact with the fingerprint sensor.

9. The wearable device of claim 8, wherein the processor is further configured to:
control the display to display a second marker for specifying a reference measurement site of the finger based on the finger being in contact with a position of the marker indicating the fingerprint sensor.

10. The wearable device of claim 9, wherein the processor is further configured to:
control the display to display text for guiding the user to move the finger in order to acquire the full fingerprint image based on the user moving the marker for specifying the reference measurement site of the finger to the reference measurement site.

11. The wearable device of claim 1, further comprising a communication interface configured to receive, from an external device, the full fingerprint image acquired in advance from the finger of the user.

12. The wearable device of claim 1, wherein the processor is further configured to:
estimate bio-information based on a pulse wave signal and a contact force based on the sensor acquiring the pulse wave signal and the contact force from the measurement site of the finger.

13. The wearable device of claim 12, wherein the bio-information comprises one or more of a blood pressure, a vascular age, an arterial stiffness, an aortic artery pressure waveform, a vascular elasticity, a stress index, and a fatigue level.

14. A method of estimating bio-information by a wearable device, comprising:
acquiring a full fingerprint image of a finger of a user based on the finger being in contact with a display of the wearable device;
acquiring a partial fingerprint image of the finger based on the finger of the user being in contact with a sensor formed on a stem disposed on a side of a main body of the wearable device; and
guiding the user, based on the partial fingerprint image acquired from the sensor and the full fingerprint image of the finger acquired from the display, to permit a measurement site of the finger to contact the sensor.

15. The method of claim 14, further comprising:
displaying the full fingerprint image of the finger and a marker indicating the measurement site of the finger on the display of the wearable device.

16. The method of claim 15, wherein the guiding comprises:
determining whether the measurement site of the finger is in contact with the sensor based on the full fingerprint image and the partial fingerprint image; and
based on determining that the measurement site of the finger is not in contact with the sensor, displaying the marker indicating a current measurement site of the finger on the full fingerprint image displayed on the display.

17. The method of claim 16, wherein the determining comprises:
determining a site matching the partial finger print image from the full fingerprint image and comparing a fingerprint image of the determined site with a fingerprint at a position where the marker indicating the measurement site is located.

18. The method of claim 16, further comprising:
guiding a contact pressure between the finger and the sensor based on determining that the measurement site of the finger is in contact with the sensor.

19. The method of claim 14, further comprising:
acquiring the full fingerprint image of the finger.

20. The method of claim 14, further comprising:
acquiring, by the sensor, a pulse wave signal and a contact force from the measurement site of the finger; and
estimating bio-information based on the acquired pulse wave signal and the acquired contact force.

21. A wearable device comprising:
a main body;
a processor configured to acquire a full fingerprint image of a finger of the user based on the finger being in contact with a display of the wearable device;
a sensor formed on a stem disposed on a side of the main body and configured to acquire a partial fingerprint image of the finger of the user based on the finger being in contact with the sensor;
a communication interface mounted in the main body; and a processor configured to:
transmit the partial fingerprint image to an external device to permit the external device to guide the user to permit a measurement site of the finger to contact the sensor, based on the partial fingerprint image acquired from the sensor, and the full fingerprint image of the finger acquired from the display; and
control the sensor to acquire a pulse wave signal based on the measurement site of the finger being in contact with the sensor.

22. The wearable device of claim 21, wherein the processor is further configured to:
estimate bio-information based on the pulse wave signal and a contact force based on the sensor acquiring the pulse wave signal and the contact force from the measurement site of the finger.

23. A wearable device comprising:
a main body;
a sensor formed on a stem disposed on a side of the main body, and configured to acquire a partial fingerprint image of a finger of a user based on the finger being in contact with the sensor; and
a processor configured to:
control a display to guide the user based on the acquired partial fingerprint image and a full fingerprint image of the finger to permit a measurement site of the finger to contact the sensor; and
acquire pulse wave signals from a plurality of target measurement sites through the sensor and determine the measurement site of the finger based on the acquired pulse wave signals.

24. The wearable device of claim 23, wherein the processor is further configured to:
control the display to display the full fingerprint image of the finger and display a marker indicating the measurement site of the finger on the displayed full fingerprint image.

25. A method of estimating bio-information by a wearable device, comprising:
acquiring a partial fingerprint image of a finger based on the finger of a user being in contact with a sensor formed on a stem disposed on a side of a main body of the wearable device;
guiding the user based on the acquired partial fingerprint image and a full fingerprint image of the finger to permit a measurement site of the finger to contact the sensor; and
determining the measurement site of the finger based on pulse wave signals acquired from a plurality of target measurement sites of the finger.

* * * * *